(12) United States Patent
Manonmani et al.

(10) Patent No.: US 6,623,932 B1
(45) Date of Patent: Sep. 23, 2003

(54) PRIMERS FOR IDENTIFYING AFLATOXINOGENIC ASPERGILLI AND AN IMPROVED METHOD THEREOF

(75) Inventors: Haravey Krishnan Manonmani, Mysore (IN); Arun Chandrashekar, Mysore (IN); Eddiya Rati Rao, Mysore (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 10/107,965

(22) Filed: Mar. 27, 2002

(51) Int. Cl.$^7$ ................................. C12Q 1/68
(52) U.S. Cl. ................ 435/6; 536/23.1; 536/24.3; 536/24.32; 536/23.7; 435/91.1
(58) Field of Search .................. 435/6, 91.1; 536/23.1, 536/24.32, 24.3, 23.7

(56) References Cited

U.S. PATENT DOCUMENTS 6,372,430 B1 * 4/2002 Morrison et al. .............. 435/6

OTHER PUBLICATIONS

Yu,J. et al. Comparison of the omtA genes encoding O–methyltransferases involved in aflatoxin biosynthesis from *Aspergillus parasiticus* and *A. flavus*. Gene 163 (1), 121–125 (1995).*

Yu,J. et al. Cloning and characterization of a cDNA from *Aspergillus parasiticus* encoding an O–methyltransferase involved in aflatoxin biosynthesis. Appl. Environ. Microbiol. 59 (11), 3564–3571 (1993).*

Yu, J. et al Genes encoding cytochrome P450 and monooxygenase enzymes define one end of the aflatoxin pathway gene cluster in *Aspergillus parasiticus*. Appl. Microbiol. Biotechnol. 53 (5), 583–590 (2000).*

Yu, J. et al Characterization of the critical amino acids of an *Aspergillus parasiticus* cytochrome P–450 monooxygenase encode by ordA that is involved in the biosynthesis of aflatoxins B1, G1, B2, and G2. Appl. Environ. Microbiol. 64 (1),4834–4841(1998).*

Watson, A. et al. Homologs of aflatoxin biosynthesis genes and sequence of aflR in Aspergillus oryzae and Aspergillus sojae, Appl. Environ. Microbiol. 65 (1), 307–310 (1999).*

Chang, P. et al. Sequence variability in homologs of the aflatoxin pathway gene aflR distinguishes species in Aspergillus section Flavi. Appl. Environ. Microbiol. 61 (1), 40–43 (1995).*

* cited by examiner

Primary Examiner—Ethan Whisenant
Assistant Examiner—Shar Hashemi
(74) Attorney, Agent, or Firm—Mathews, Collins, Shepherd & McKay. P.A.

(57) ABSTRACT

The present invention relates to three sets of novel primers of SEQ ID Nos. 1–6, wherein said three sets of primer are designed from three genes omt, ord, and afl R respectively of aflatoxin biosynthesis pathway of fungi *Aspergillus flavus* and an improved method of identifying aflatoxinogenic aspergilli using said three sets of primers.

27 Claims, 2 Drawing Sheets

PRIMERS FOR IDENTIFYING AFLATOXINOGENIC ASPERGILLI AND AN IMPROVED METHOD THEREOF

FIELD OF THE PRESENT INVENTION

The present invention relates to three sets of novel primers of SEQ ID Nos. 1–6, wherein said three sets of primer are designed from three genes omt, ord, and afl R respectively of aflatoxin biosynthesis pathway of fungi *Aspergillus flavus* and an improved method of identifying aflatoxinogenic aspergilli using said three sets of primers.

BACKGROUND OF THE PRESENT INVENTION

Aflatoxins are potent carcinogenic, mutagenic and teratogenic metabolites produced primarily by the fungal species of *Aspergillus flavus* and *Aspergillus parasiticus*. Foods and feeds, especially in warm climates are susceptible to invasion by aflatoxigenic Aspergillus sp. And subsequent production of Aflatoxins during preharvesting, processing, transportation or storage. Over the last few years, means for mycotoxin detection have been simplified, by the adoption of immunological methods. The level of mold infestation and identification of the governing species are important parameters which could give an indication of the quality of the material and future potential for the presence of mycotoxins.

Mold counts are a part of quality control assurance for foods. This method is time consuming, labour intensive, costly requires facilities and mycological expertise and do not allow the specification of mycotoxegenic fungi.

With the advances made in the detection methods, polymerase chain reaction (PCR) facilitates in vitro amplification of target sequence and offers several advantages over traditional methods of detection.

Reference may be made to the work of Miller and Martin (1988) for the application of PCR techniques for the detection of microorganisms, including plant pathogens. However no attempt has been made to detect aflatoxin-producing fungi.

Reference may be made to the works of Payne and Woloshuk (1989) and Nu, et al (1995). Who have identified the genes in Aflatoxins biosynthetic pathway of strains of *A. flavus* and *A. parasiticus*. However, detection of aflatixigenic fungi were not attempted.

Reference may be made to the work of Shapira, et al (1996), where in the identification of aflatoxin producing molds in grains has been attempted using PCR techniques. Three genes ver-1, omt-1 and apa-2 coding for key enzymes and regulatory factor in biosynthesis of aflatoxin were used as primers. Positive results were obtained in 24 h enriched cultures at lowest spore level of $10^2$ spores per gram. However incubation of dried ground corn seeds in enrichment media allowed detection as few as $10^2$ spores per gram after 48 h of incubation.

The drawback of these references is that no attempts have been made to detect aflatoxigenic fungi and the traditional methods are non-sensitive, time consuming and lack consistency. The present invention enables detection of aflatoxigenic fungi by PCR using specific aflatoxin biosynthetic pathway genes. This method has application in food system.

OBJECTS OF THE PRESENT INVENTION

The main object of the present invention is to develop primers from genes of aflatoxin biosynthesis pathway.

Another main object of the present invention is to develop primers for genes omt, ord, and afl R of aflatoxin biosynthesis pathway.

Yet another object of the present invention is to develop an improved method for identifying aflatoxinogenic aspergilli.

Still another object of the present invention is to develop an improved method for identifying aflatoxinogenic aspergilli using said primers.

Still another object of the present invention is to develop a method of identifying aflatoxinogenic aspergilli directly in food articles.

Still another object of the present invention is to develop a highly sensitive method to identifying aflatoxinogenic aspergilli.

Further object of the present invention is to develop an identification method using multiple number of primers for more accuracy.

SUMMARY OF THE PRESENT INVENTION

The present invention relates to three sets of novel primers of SEQ ID Nos. 1–6, wherein said three sets of primer are designed from three genes omt, ord, and afl R respectively of aflatoxin biosynthesis pathway of fungi *Aspergillus flavus* and an improved method of identifying aflatoxinogenic aspergilli using said three sets of primers.

DETAILED DESCRIPTION OF THE PRESENT INVENTION

Accordingly, the present invention relates to three sets of novel primers of SEQ ID Nos. 1–6, wherein said three sets of primer are designed from three genes omt, ord, and afl R respectively of aflatoxin biosynthesis pathway of fungi *Aspergillus flavus* and an improved method of identifying aflatoxinogenic aspergilli using said three sets of primers.

In one embodiment of the present invention, three sets of oligonucleotide primers of SEQ ID Nos. 1 through 6. (Please refer sequences shown below).

omt 1 (F) 5' AGCGTCCGAATCCCTTTAAT 3' (SEQ ID NO. 1)
(R) 5' AGGGTGTTCGCCAATCATAG 3' (SEQ ID NO. 2)

ord (F) 5' ACTGCCCCTCAGCTAACCTC 3' (SEQ ID NO. 3)
(R) 5' GCATCAGCATTCTTCCAAGG 3' (SEQ ID NO. 4)

aflR (F) 5' AACCGCATCCACAATCTCAT 3' (SEQ ID NO. 5)
(R) 5' AGTGCAGTTCGCTCAGAACA 3' (SEQ ID NO. 6)

In further embodiment of the present invention, said three sets of primer of SEQ ID Nos. 1–6 used together shows more accurate identification as compared to any one set of primer alone.

In another embodiment of the present invention, wherein said primers are designed from genes of aflatoxin biosynthesis pathway of fungi *Aspergillus flavus*.

In yet another embodiment of the present invention, wherein said primers are designed for three specific genes omt, ord, and afl R.

In still another embodiment of the present invention, wherein primers 1 and 2 correspond to gene omt encoding o-methyl transferase.

In still another embodiment of the present invention, wherein primers 3 and 4 correspond to gene ord encoding oxidoreductase.

In still another embodiment of the present invention, wherein primers 5 and 6 correspond to gene afl R encoding aflatoxin regulatory protein.

In still another embodiment of the present invention, wherein primers 1, 3, and 5 are forward primers.

In still another embodiment of the present invention, wherein primers 2, 4, and 6 are reverse primers.

In still another embodiment of the present invention, wherein length of primers is 20 base pairs (bp).

In further embodiment of the present invention, sequences of three genes omt, ordA, and afl R are as follows:

A. O methyltransferase (Omt) gene from the published gene sequence with Accession no L25834 where the primers covers the region between 1811 to 2218 with the product size 407 bp of SEQ ID NO. 7.

B. Oxidoreductase (ord) gene from the published gene sequence with Accession no AF 169016 where the primer covers the region between 3142 to 3530 with product size 388 bp of SEQ ID NO. 8.

C. Aflotoxin regulatory gene (aflR) from the published gene sequence with Accession no AF 264763 where the said primer covers the region between 540 to 1338 with the product size 798 bp of SEQ ID NO. 9.

In further embodiment of the present invention, an improved method of identifying aflatoxigenic aspergilli using primers of claim 1 independently or in combination.

In another embodiment of the present invention, harvesting mixed microflora from food system.

In yet another embodiment of the present invention, extracting DNA from said harvested flora. (Please refer FIGS. 1, and 2)

BRIEF DESCRIPTION OF THE ACCOMPANYING DRAWINGS

Figure 1:
FIG. 1 shows amplicons from the PCR with three sets of primers from DNA of *Aspergillus flavus* ATCC 46283. a, b, c, d, , DNA isolated from samples harvested at 12,24,36 and 48 hours and amplified with primers for the aflR gene.
Figure 2:
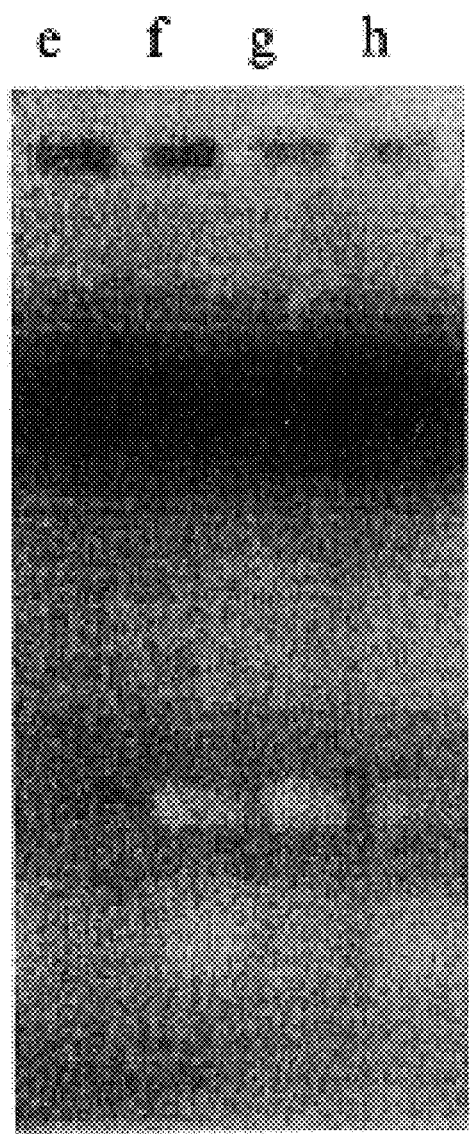
FIG. 2 shows amplicons from the PCR with three sets of primers from DNA of *Aspergillus flavus* ATCC 46283. e, f, g, h DNA isolated from samples harvested at 12,24,36 and 48 hours and amplified with primers for the omt gene In still another embodiment of the present invention, amplifying DNA by PCR using said primers. (Please refer FIGS. 1, and 2)

In still another embodiment of the present invention, analyzing amplified DNA by electrophoresis.

In still another embodiment of the present invention, identifying aflatoxigenic fungi.

In still another embodiment of the present invention, wherein fungi are harvested by centrifugation.

In still another embodiment of the present invention, wherein DNA is extracted using mixture of phenol, chloroform, and amyl alcohol in ratio of about 25:24:1.

In still another embodiment of the present invention, wherein primers are designed using software programme Primer 3.0.

In still another embodiment of the present invention, wherein primers 1 and 2 amplify 406 base pairs (bp) fragment of gene omt.

In still another embodiment of the present invention, wherein primers 3 and 4 amplify 387 base pairs (bp) fragment of gene ord.

In still another embodiment of the present invention, wherein primers 5 and 6 amplify 1299 base pairs (bp) fragment of gene afl R.

In still another embodiment of the present invention, wherein amplification mixture for amplifying DNA comprises Tris-HCl, Potassium Chloride (KCl), Magnesium Chloride ($MgCl_2$), gelatin, deoxyribonucleoside triphosphates, primers, Taq DNA polymerase, and sterile ultra filtered water.

In still another embodiment of the present invention, wherein electrophorizing amplified DNA using agarose gel.

In still another embodiment of the present invention, wherein said method identifies aflatoxigenic fungi as young as 12 hrs old.

In still another embodiment of the present invention, wherein said method is particularly useful in detecting aflatoxigenic *Aspergillus flavus,* and *Aspergillus parasiticus.*

In still another embodiment of the present invention, wherein said method detects aflatoxigenic fungi directly in food grains.

In still another embodiment of the present invention, wherein said method detects aflatoxigenic fungi from $10^{-2}$ to $10^{-6}$ cell numbers in grains.

In still another embodiment of the present invention, wherein said method extracts DNA without using liquid nitrogen.

In still another embodiment of the present invention, said method with three sets of primer use together shows more accurate identification as compared to any one set of primer alone.

Accordingly, the present invention provides an improved method for the detection of aflatoxigenic molds in food systems which comprises:

a). Designing a set of novel nucleotide primers for o-methyl transferase, oxidoreductase and aflatoxin regulatory genes in *Aspergillus flavus* which may be selected from the sequence of omt 1 (F) 5' AGCGTCCGAATCCCTTTAAT 3' (SEQ ID NO. 1)

(R) 5' AGGGTGTTCGCCAATCATAG 3' (SEQ ID NO. 2)

ord (F) 5' ACTGCCCCTCAGCTAACCTC 3' (SEQ ID NO. 3)

(R) 5' GCATCAGCATTCTTCCAAGG 3' (SEQ ID NO. 4)

aflR (F) 5' AACCGCATCCACAATCTCAT 3' (SEQ ID NO. 5)

(R) 5' AGTGCAGTTCGCTCAGAACA3' (SEQ ID NO. 6)

b). A method for detection of aflatoxigenic fungi using primers specific for omt, ord and afl R gene in a mixed microflora.

c). Extraction of template DNA from moulds in grains or other food commodities.

d). Extraction of template DNA from *Aspergillus flavus, Aspergillus parasiticus* and Fusarium sp. may be effected by grinding the fungal mass in Tris - EDTA (50 mM:5 mM) buffer containing % sodium dodocyl sulphate (SDS), followed by extraction using phenol:isoamyl alcohol at 25:24:01.

e). The PCR reaction mixture in a total volume of 25 $\mu$l may consist of buffer 2.5 $\mu$l ,d NTP mix 0.5 $\mu$l, taq - polymerase 0.3 $\mu$l, water 18.78 $\mu$l, each specific primer—forward 1 $\mu$l, reverse 1 $\mu$l and template DNA 1 $\mu$l.

f) Detection of aflatoxigenic fungi by amplification of target gene may be effected from an initial denaturation at 90°–98° C. for 2–8 min, amplification cycle of 28 to 40, each cycle with a denaturation at 90°–98° C. for 40–70 secs, annealing at 46°–62° C. for 40–80 secs and an extension at 68°–76° C. for 4 to 12 min.

g). The analysis of the PCR product may be achieved in 1.2–1.8% agarose gel electrophoresis, visualization of PCR product by staining with 0.5 µg/ml ethidium bromide and observation in a UV - transilluminator.

i). Detection of time course may be effected indicating the rapidity of detection.

j). Detection of aflatoxigenic moulds amongst different moulds may be effected indicating high sensitivity of the reaction.

In an embodiment of the present invention, effective amplification of o-methyl transferase, oxidoreductase and aflatoxin regulatory genes may be effected at initial denaturation at 93°–95° C. for 4–6 min, amplification cycles of 32–38, each cycle with a denaturation at 93°–95° C. for 55–65 seconds annealing at 48°–52° C. for 55–65 seconds and an extension at 70°–74° C. for 55–65 seconds and a final extension at 68°–76° C. for 6–10 min.

In another embodiment of the present invention, the PCR method can detect from 12 to 120 h old mycelia.

In yet another embodiment of the present invention, the PCR method may detect toxigenic fungi directly in grains.

The patent relates to PCR method for the detection of aflatoxigenic fungi. Polymerase chain reaction method was used to selectively amplify o-methyl transferase, oxidoreductase and aflatoxin regulatory genes in toxigenic fungi. Fungi grown in czapek-dox or potato dextrose broth or from contaminated grains were used for the isolation of template DNA. The PCR reaction mixture and amplification conditions were optimized for specific amplification. Visualization of PCR products revealed that by the method followed, it is possible to detect toxigenic fungi from $10^{-2}$ to $10^{-6}$ cell numbers in grains and only from aflatoxigenic fungi.

The novelty of this method is the use of the designed primers for the direct detection of aflatoxigenic moulds by PCR. This method can detect aflatoxigenic fungi from contaminated grains. The method is rapid and sensitive making it possible to detect aflatoxigenic fungi from contaminated food systems without culturing them.

The following examples are given by way of illustrations of the present invention and therefore should not be construed to limit the scope of the present invention.

EXAMPLE 1

Oligonucleotide primers for o-methyltransferase, oxidoreductase, and aflatoxin regulatory gene of *Aspergillus flavus* were designed based on the gene sequence (ENTREZ) using the software programme primer 3.0. These primer sets amplify 406, 387 and 1299 base pair (bp) respectively fragment of the gene, the sequence of which is given below. Sterilization of media and other solutions was achieved by autoclaving for 20 min. at 121° C.

omt 1 (F) 5' AGCGTCCCAATCCCTTTAAT 3' (SEQ ID NO. 1)
omt 2 (R) 5' AGGGTGTTCGCCAATCATAG 3' (SEQ ID NO. 2)

ord 1 (F) 5' ACTGCCCCTCAGCTAACCTC 3' (SEQ ID NO. 3)
ord 2 (R) 5' GCATCAGCATTCTTCCAAGG 3' (SEQ ID NO. 4)

aflR 1 (F) 5' AACCGCATCCACA ATCTCAT 3' (SEQ ID NO. 5)
afl R 2 (R) 5' AGTGCAGTTCGCTCAGAACA3' (SEQ ID NO. 6)

EXAMPLE 2

Oligonucleotide primers for o-methyltransferase, oxidoreductase, and aflatoxin regulatory gene of *Aspergillus flavus* were designed based on the gene sequence (ENTREZ) using the software programme primer 3.0. These primer sets amplify 406, 387, and 1299 base pair (bp) fragment of the gene, the sequence of which is given below. Sterilization of media and other solutions was achieved by autoclaving for 20 min. at 121° C.

omt 1 (F) 5' AGCGTCCGAATCCCTTTAAT 3' (SEQ ID NO. 1)
omt 2 (R) 5' AGGGTGTTCGCCAATCATAG 3' (SEQ ID NO. 2)

ord 1 (F) 5' ACTGCCCCTCAGCTAACCTC 3' (SEQ ID NO. 3)
ord 2 (R) 5' GCATCAGCATTCTTCCAAGG 3' (SEQ ID NO. 4)

aflR 1 (F) 5' AACCGCATCCACA ATCTCAT 3' (SEQ ID NO. 5)
afl R 2 (R) 5' AGTGCAGTTCGCTCAGAACA 3' (SEQ ID NO. 6)

EXAMPLE 3

Oligonucleotide primers for o-methyltransferase, oxidoreductase, and aflatoxin regulatory gene of *Aspergillus flavus* were designed based on the gene sequence (ENTREZ) using the software programme primer 3.0. These primer sets amplify 406, 387, and 1299 base pair (bp) fragment of the gene, the sequence of which is given below. Sterilization of media and other solutions was achieved by autoclaving for 20 min. at 121° C.

omt 1 (F) 5' AGCGTCCGAATCCCTTTAAT 3' (SEQ ID NO. 1)
omt 2 (R) 5' AGGGTGTTCGCCAATCATAG 3' (SEQ ID NO. 2)

ord 1 (F) 5' ACTGCCCCTCAGCTAACCTC 3' (SEQ ID NO. 3)
ord 2 (R) 5' GCATCAGCATTCTTCCAAGG 3' (SEQ ID NO. 4)

aflR 1 (F) 5' AACCGCATCCACA ATCTCAT 3' (SEQ ID NO. 5)
af R 2 (R) 5' AGTGCAGTTCGCTCAGAACA 3' (SEQ ID NO. 6)

EXAMPLE 4

Oligonucleotide primers for o-methyltransferase, oxidoreductase, and aflatoxin regulatory gene of *Aspergillus flavus* were designed based on the gene sequence (ENTREZ) using the software programme primer 3.0. These primer sets amplify 406, 387, and 1299 base pair (bp) fragment of the gene, the sequence of which is given below. Sterilization of media and other solutions was achieved by autoclaving for 20 min. at 21° C.

omt 1 (F) 5' AGCGTCCGAATCCCTTTAAT 3' (SEQ ID NO. 1)

omt 2 (R) 5' AGGGTGTTCGCCAATCATAG 3' (SEQ ID NO. 2)

ord 1 (F) 5' ACTGCCCCTCAGCTAACCTC 3' (SEQ ID NO. 3)

ord 2 (R) 5' GCATCAGCATTCTTCCAAGG 3' (SEQ ID NO. 4)

aflR 1 (F) 5' AACCGCATCCACA ATCTCAT 3' (SEQ ID NO. 5)

aflR 2 (R) 5' AGTGCAGTTCGCTCAGAACA 3' (SEQ ID NO. 6)

One ml spore suspensions of 27 different fungi, belonging to Fusarium spp (6 no.), *Aspergillus flavus* (6 nos.), *Aspergillus parasiticus.*(3nos.), Aspergillus spp, (4 nos.), *Aspergillus oryzae* (3 nos.), Rhizopus spp (3 nos.) were inoculated to potato - dextrose broth and incubated at ambient temperatures (26°–28° C.) under stationary conditions for 96 h. DNA was extracted from ground mycelia without liquid nitrogen treatment.

Amplification was performed in a total reaction volume of 25 µl which contained 1× PCR buffer (10 mM Tris-HCl, pH 9.0, 50 mM KCl, 1.5 mM $MgCl_2$, 0.01% gelatin), each of deoxyribonucleoside triphosphate,4 nm of each primer and unit of taq DNA polymerase and sterile ultra filtered water. Template DNAs were initially denatured at 94° C. for 4 min. Subsequently, a total of 35 amplification cycles were carried out in a programmable thermocycler. Each cycle consisted of denaturation for 30 sec. At 94° C., primer annealing for 45 secs. at 50° C. and an extension for 1.15 min. at 72° C. The last cycle was followed by a final extension at 72° C. for 10 min.

PCR products were analysed by agarose gel electrophoresis. Aliquots of 10 µl PCR products were mixed with 2.0 µl of loading dye and loaded on to 1.2% agarose gel and subjected to electrophoresis for 2 h at 100 volts in 1× TAE buffer. Gel was stained with ethidium bromide (0.5 µg/ml), destained with distilled water and examined on a UV transilluminator. A 100 bp ladder was used as a molecular size marker. The amplification profile in the gel was documented in a CCL camera based gel documentation system.

The template DNA from Rhizopus 3 spp (2) *Aspergillus flavus* (2), Fusarium strains (6) and Aspergillus (4), *Aspergillus oryzae* (5) strains did not show any amplification. However, toxin producing *Aspergillus flavus* (4) and *Aspergillus parasiticus* (3) showed amplifications.

The main advantages of the present invention are:

1. The designed o-methyltransferase, oxidoreductase, and aflatoxin regulatory primers are specific for the detection of aflatoxigenic fungi.
2. The designed primers can detect aflatoxigenic fungi even at 24 h of growth.
3. The designed primers can specifically detected fungi possessing aflatoxin-producing genes.
4. A simple and effective method has been used for the isolation of template DNA without the application of liquid nitrogen.

Sequences of three genes omt, ordA, and afl R.

A. O methyltransferase (Omt) gene from the published gene sequence with Accession no L25834 where the primers covers the region between 1811 to 2218 with the product size 407 bp of SEQ ID NO. 7.

L25834. Aspergillus paras . . . omt gene [gi:414297]
1811 agcgtccgaatccctttaat ttgcttcgat ggctaattgt tccaacagtg
1861 catgcgtgga aatcctctcc aacatcgtca ccgccatgga cccaag-
caag tcgcgcatcc
1921 ttctggacga aatgattatg cccgatcttt tggcgcagga ttcg-
cagcgc ttcatgaatc
1981 agatcgacat gactgttgtt ctgacattga acgggaagga gaggtc-
tacc aaggagtgga
2041 attcgcttat tacgacggta gatggtagac tggagactga gaa-
gatatgg tggcgcaaag
2101 gcgaggaagg gtctcactgg ggcgttcaac aactgcgttt gcg-
caagtag gggaatgcaa
2161 tggagatatc cttgggtctg tcagaagaac ggctgag ctatgattg-
gcgaacaccct 2218

B. Oxidoreductase (ord) gene from the published gene sequence with Accession no AF 169016 where the primer covers the region between 3142 to 3530 with product size 388 bp of SEQ ID NO. 8.

ACCESSION AF169016
VERSION AF169016.1 GI:6715098 *Aspergillus parasiticus* oxidoreductase (ordA), versicolorin B synthase (vbs), cytochrome P450 monooxigenase (cypX), and monooxigenase (moxY) genes, complete cds 3142 actgcccct cagctaacct catactaatt aggacgttta
3181 cccatgatcc cagtgtctac cacgacccaa tggtgttcaa gcca-
gagcga ttcctggagc
3241 gacaaagctc cccgccggaa acggatccca tgaaatttgt gttcg-
gcttt gggcgtcgta
3301 tatgccccgg tcggtttgta acagacgaaa agctattttt gat-
tgcgtgc cacgccatca
3361 gttgcttctt gatctcgccc aaggatccag gagctccgga
acccgactgg ttgccgggcg
3421 tcatcagtca accgggcccc tttgacctca atgtggtgcc tcgcagc-
cct gctcacgaag
3481 aattgattcg ttcaatcgag acggaccat ccttggaagaatgct-
gatgc 3530

C. Aflotoxin regulatory gene (aflR) from the published gene sequence with Accession no AF 264763 where the said primer covers the region between 540 to 1338 with the product size 798 bp of SEQ ID NO. 9.

*Aspergillus sojae* strain ATCC 42251 AFLR regulatory protein (aflR) gene, complete cds.

ACCESSION AF264763 VERSION AF264763.1 GI:8572226

540 aaccgcatcca caatctcatc ctcaatcgaa tcaaccacca
cacgctctgc ccaccccaa
601 tggtagcagt agcgtctccg ccatctttc tcaccagagt cccccgc-
cac tcgtggagac
661 ccagggcctt ggaggagatc tggctggtca ggcgcaaagc accct-
gtctt ccctaacagt
721 cgattcggaa ttcggggggct cttttgcagtc aatggaacac ggaaac-
catg ccgatttctt
781 ggcggagtcg acggggagtc ttttcgacgc gttttggaa gtggg-
gaccc ccatgatcga
841 cccgttcctc gagtcggccc cactgccacc gtttcaggcg cgctat-
tgct gcttttcgct
901 agcactacaa acactgacct gcctcttccc ccacgccccg ctgggct-
gtc agctgcggct
961 gacggacggt gaggacagtt cgtgcaacct gatgacgact gatatg-
gtca tctcgggaa
1021 caagaaggct accgatgcgg tccggaagat cctcgggtgt tcgt-
gcgcgc aggatggcta
1081 cttgctgagc atggtcgtcc ttatcgttct caaggtgctg gggtgg-
tatg ctgcggcagc
1141 aggcaccag tgtacctcaa cggcggcggg tggagaaacc
aacagtggca gctgtagcaa 1201 cagtcccgcc accgtgtcca gtggctgtct gacggaagag cgcgtgctgc accaccctag
1261 tatggtgggc gaggattgtg tggatgagga agaccagccg cgagtggcgg cacagcttgt
1321 tctgagcgaactgcact 1338

---

What is claimed is:

1. Three sets of oligonucleotide primers of SEQ ID Nos. 1 through 6.

2. Primers as claimed in claim 1, wherein said primers are designed from genes of aflatoxin biosynthesis pathway of fungi *Aspergillus flavus*.

3. Primers as claimed in claim 2, wherein said primers are designed for three specific genes omt, ord, and afl R.

4. Primers as claimed in claim 1, wherein primers 1 and 2 correspond to gene omt encoding o-methyl transferase.

5. Primers as claimed in claim 4, wherein said primers cover the region between 1811 to 2218 in gene omt with the product size of 407 bp.

6. Primers as claimed in claim 1, wherein primers 3 and 4 correspond to gene ord encoding oxidoreductase.

7. Primers as claimed in claim 6, wherein said primers cover the region between 3142 to 3530 in gene ord with the product size of 388 bp.

8. Primers as claimed in claim 1, wherein primers 5 and 6 correspond to gene afl R encoding aflatoxin regulatory protein.

9. Primers as claimed in claim 8, wherein said primers cover the region between 540 to 1338 in gene aflR with the product size of 798 bp.

10. Primers as claimed in claim 1, wherein primers 1, 3, and 5 are forward primers.

11. Primers as claimed in claim 1, wherein primers 2, 4, and 6 are reverse primers.

12. Primers as claimed in claim 1, wherein length of primers is 20 base pairs (bp).

13. An improved method of identifying aflatoxigenic aspergilli using primers of claim 1 independently or in combination, said method comprising steps of:

(a) harvesting mixed microflora from food system, (b) extracting DNA from said harvested flora, (c) amplifying DNA by PCR using said primers, (d) analyzing amplified DNA by electrophoresis, and (e) identifying aflatoxigenic fungi.

14. A method as claimed in claim 13, wherein fungi are harvested by centrifugation.

15. A method as claimed in claim 13, wherein DNA is extracted using mixture of phenol, chloroform, and amyl alcohol in ratio of about 25:24:1.

16. A method as claimed in claim 13, wherein primers are designed using software programme Primer 3.0.

17. A method as claimed in claim 13, wherein primers 1 and 2 amplify 406 base pairs (bp) fragment of gene omt.

18. A method as claimed in claim 13, wherein primers 3 and 4 amplify 387 base pairs (bp) fragment of gene ord.

19. A method as claimed in claim 13, wherein primers 5 and 6 amplify 1299 base pairs (bp) fragment of gene afl R.

20. A method as claimed in claim 13, wherein amplification mixture for amplifying DNA comprises Tris-HCl, Potassium Chloride (KCl), Magnesium Chloride ($MgCl_2$), gelatin, deoxyribonucleoside triphosphates, primers, Taq DNA polymerase, and sterile ultra filtered water.

21. A method as claimed in claim 13, wherein electrophorizing amplified DNA using agarose gel.

22. A method as claimed in claim 13, wherein said method identifies aflatoxigenic fungi as young as 12 hrs old.

23. A method as claimed in claim 13, wherein said method is particularly useful in detecting aflatoxigenic *Aspergillus flavus,* and *Aspergillus parasiticus.*

24. A method as claimed in claim 13, wherein said method detects aflatoxigenic fungi directly in food grains.

25. A method as claimed in claim 13, wherein said method detects aflatoxigenic fungi from $10^{-2}$ to $10^{-6}$ cell numbers in grains.

26. A method as claimed in claim 13, wherein said method extracts DNA without using liquid nitrogen.

27. A method as claimed in claim 13, wherein said method with three sets of primer used together shows more accurate identification as compared to any one set of primer alone.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Aspergillus sojae

<400> SEQUENCE: 1
agcgtccgaa tccctttaat                                           20

<210> SEQ ID NO 2
<211> LENGTH: 20
<212> TYPE: DNA
<213> ORGANISM: Aspergillus sojae

<400> SEQUENCE: 2
agggtgttcg ccaatcatag                                           20

<210> SEQ ID NO 3
<211> LENGTH: 20
<212> TYPE: DNA
<213> ORGANISM: Aspergillus sojae

<400> SEQUENCE: 3
actgcccctc agctaacctc                                           20

<210> SEQ ID NO 4
<211> LENGTH: 20
<212> TYPE: DNA
<213> ORGANISM: Aspergillus sojae

<400> SEQUENCE: 4
gcatcagcat tcttccaagg                                           20

<210> SEQ ID NO 5
<211> LENGTH: 20
<212> TYPE: DNA
<213> ORGANISM: Aspergillus sojae

<400> SEQUENCE: 5
aaccgcatcc acaatctcat                                           20

<210> SEQ ID NO 6
<211> LENGTH: 20
<212> TYPE: DNA
<213> ORGANISM: Aspergillus sojae

<400> SEQUENCE: 6
agtgcagttc gctcagaaca                                           20

<210> SEQ ID NO 7
<211> LENGTH: 407
<212> TYPE: DNA
<213> ORGANISM: Aspergillus sojae

<400> SEQUENCE: 7
agcgtccgaa tccctttaat ttgcttcgat ggctaattgt tccaacagtg catgcgtgga    60

-continued

| | |
|---|---|
| aatcctctcc aacatcgtca ccgccatgga cccaagcaag tcgcgcatcc ttctggacga | 120 |
| aatgattatg cccgatcttt tggcgcagga ttcgcagcgc ttcatgaatc agatcgacat | 180 |
| gactgttgtt ctgacattga acgggaagga gaggtctacc aaggagtgga attcgcttat | 240 |
| tacgacggta gatggtagac tggagactga aagatatgg tggcgcaaag gcgaggaagg | 300 |
| gtctcactgg ggcgttcaac aactgcgttt gcgcaagtag gggaatgcaa tggagatatc | 360 |
| cttgggtctg tcagaagaac ggctgagcta tgattggcga acaccct | 407 |

<210> SEQ ID NO 8
<211> LENGTH: 388
<212> TYPE: DNA
<213> ORGANISM: Aspergillus sojae

<400> SEQUENCE: 8

| | |
|---|---|
| actgcccctc agctaacctc atactaatta ggacgtttac ccatgatccc agtgtctacc | 60 |
| acgacccaat ggtgttcaag ccagagcgat tcctggagcg acaaagctcc ccgccggaaa | 120 |
| cggatcccat gaaatttgtg ttcggctttg ggcgtcgtat atgccccggt cggtttgtaa | 180 |
| cagacgaaaa gctattttg attgcgtgcc acgccatcag ttgcttcttg atctcgccca | 240 |
| aggatccagg agctccggaa cccgactggt tgccgggcgt catcagtcaa ccgggcccct | 300 |
| ttgacctcaa tgtggtgcct cgcagccctg ctcacgaaga attgattcgt tcaatcgaga | 360 |
| cggaccatcc ttggaagaat gctgatgc | 388 |

<210> SEQ ID NO 9
<211> LENGTH: 798
<212> TYPE: DNA
<213> ORGANISM: Aspergillus sojae

<400> SEQUENCE: 9

| | |
|---|---|
| aaccgcatcc acaatctcat cctcaatcga atcaaccacc acacgctctg cccaccccca | 60 |
| atggtagcag tagcgtctcc gccatctttt ctcaccagag tcccccgcca ctcgtggaga | 120 |
| cccagggcct tggaggagat ctggctggtc aggcgcaaag caccctgtct tccctaacag | 180 |
| tcgattcgga attcggggc tctttgcagt caatggaaca cggaaaccat gccgatttct | 240 |
| tggcggagtc gacggggagt cttttcgacg cgttttttgga agtggggacc cccatgatcg | 300 |
| acccgttcct cgagtcggcc ccactgccac cgtttcaggc gcgctattgc tgcttttcgc | 360 |
| tagcactaca aacactgacc tgcctcttcc cccacgcccc gctgggctgt cagctgcggc | 420 |
| tgacggacgg tgaggacagt tcgtgcaacc tgatgacgac tgatatggtc atctcgggga | 480 |
| acaagaaggc taccgatgcg gtccggaaga tcctcgggtg ttcgtgcgcg caggatggct | 540 |
| acttgctgag catggtcgtc cttatcgttc tcaaggtgct ggggtggtat gctgcggcag | 600 |
| caggcaccca gtgtacctca acggcggcgg gtggagaaac caacagtggc agctgtagca | 660 |
| acagtcccgc caccgtgtcc agtggctgtc tgacggaaga gcgcgtgctg caccacccta | 720 |
| gtatggtggg cgaggattgt gtggatgagg aagaccagcc gcgagtggcg gcacagcttg | 780 |
| ttctgagcga actgcact | 798 |